United States Patent [19]

Bremer et al.

[11] Patent Number: 4,525,471

[45] Date of Patent: Jun. 25, 1985

[54] ATTRITION RESISTANT MICROSPHEROIDAL FLUID BED CATALYSTS CONTAINING THE MIXED OXIDES OF VANADIUM AND PHOSPHORUS

[75] Inventors: Noel J. Bremer, Kent; Dennis E. Dria, Cleveland Heights; Patricia R. Blum, Macedonia; Ernest C. Milberger, Solon; Mark L. Nicholas, Cleveland, all of Ohio

[73] Assignee: The Standard Oil Company, Cleveland, Ohio

[21] Appl. No.: 594,959

[22] Filed: Apr. 2, 1984

Related U.S. Application Data

[63] Continuation of Ser. No. 422,120, Sep. 23, 1982, abandoned.

[51] Int. Cl.$^3$ .............................................. B01J 27/14
[52] U.S. Cl. .................................. 502/209; 502/210; 502/211; 502/212; 502/213
[58] Field of Search ............... 502/209, 210, 211, 212, 502/213; 252/435, 437

[56] References Cited

U.S. PATENT DOCUMENTS

| | | | |
|---|---|---|---|
| 3,478,063 | 11/1969 | Friedrichsen et al. | 252/435 X |
| 3,625,863 | 12/1971 | Heller et al. | 252/437 |
| 3,832,359 | 8/1974 | Freeks et al. | 252/437 X |
| 3,867,411 | 2/1975 | Roffelson et al. | 252/437 |
| 3,888,886 | 6/1975 | Young et al. | 252/435 X |
| 3,975,300 | 8/1976 | Burress | 252/435 |
| 4,049,574 | 9/1977 | Kerr et al. | 252/437 |
| 4,092,332 | 5/1978 | Freeks et al. | 252/437 X |
| 4,222,945 | 9/1980 | Higgins et al. | 252/437 X |
| 4,317,778 | 3/1982 | Blum | 502/209 X |
| 4,333,853 | 6/1982 | Milberger et al. | 252/437 X |
| 4,351,773 | 9/1982 | Milberger et al. | 252/437 X |
| 4,410,752 | 10/1983 | Blum et al. | 502/209 |

Primary Examiner—William G. Wright
Attorney, Agent, or Firm—David P. Yusko; John E. Miller, Jr.; Larry W. Evans

[57] ABSTRACT

A process is provided for the preparation of attrition resistant, microspheroidal fluid bed catalysts comprising the mixed oxides of vanadium and phosphorus in which a vanadium phosphorus mixed oxided catalyst precursor is densified, comminuted, formed into fluidizable particles and calcined under fluidization-type conditions. The present invention further provides the attrition resistant fluidizable catalysts prepared by the inventive process, and further provides a process for utilizing such attrition resistant catalysts in the production of maleic anhydride in the vapor phase by the oxidation of 4 carbon atom hydrocarbons.

20 Claims, No Drawings

ATTRITION RESISTANT MICROSPHEROIDAL FLUID BED CATALYSTS CONTAINING THE MIXED OXIDES OF VANADIUM AND PHOSPHORUS

REFERENCE TO RELATED APPLICATIONS

This is a continuation of application Ser. No. 422,120 filed Sept. 23, 1982, now abandoned.

BACKGROUND OF THE INVENTION

This invention relates to a method for preparing attrition resistant fluid bed catalysts useful in the production of dicarboxylic acid anhydrides by the oxidation of hydrocarbons. More particularly it is directed to the preparation of fluid bed catalysts suitable for producing maleic anhydride from 4-carbon atom hydrocarbons, such as n-butane, n-butenes, 1,3 butadiene or a mixture thereof.

The advantages of fluid bed hydrocarbon oxidation processes compared to fixed bed hydrocarbon oxidation processes are well known in the art, including the improvement of temperature control and heat transfer for oxidation reactions. Catalysts which are suitable for fixed bed processes, however, are not necessarily suitable for fluid bed processes. Catalysts which are suitable for fixed bed processes in which there are few attritting forces in operation may be too "soft" to withstand the attrition caused by fluid bed operation.

Attrition of the catalyst in fluid bed operations, that is, the removal of the outer layer of the catalyst particle by abrasion or the breakup or fracture of the catalyst particle is caused by impact of the fluidized particles with each other, with the walls of the fluid bed vessel, especially within the reactor cyclones which trap the fluidized catalyst particles before they escape the reactor to return the particles to the catalyst bed.

Catalysts containing vanadium and phosphorus oxides have been used in the oxidation of 4-carbon atom hydrocarbons, such as n-butane, n-butenes, 1,3 butadiene or mixtures thereof with molecular oxygen or oxygen-containing gas to produce maleic anhydride. Conventional methods of preparing these catalysts involve reducing a pentavalent vanadium compound, and combining the same with a phosphorus compound, and if desired, promoter element compounds under conditions which will provide vanadium in a valence state below +5 to form catalyst precursors capable of being converted to an oxide. The catalyst oxide precursor is then recovered and calcined, before or after the fixed bed catalyst particles are formed, to provide active catalytic material.

U.S. Pat. Nos. 3,888,886; 3,905,914; 3,931,046; 3,932,305 and 3,975,300 disclose the testing of promoted vanadium phosphorus oxide catalysts for maleic anhydride production from butane in one inch diameter fluid bed reactors. In most instances, the catalysts were prepared by forming the catalyst precursor in aqueous media (in U.S. Pat. No. 3,975,300 the precursor was formed in a paste of a vanadium compound, a phosphorus compound and an organic reducing agent), drying and thereafter grinding and sieving the precursor to a powder of about 74 to 250 microns size. This manner of preparation, however, does not obtain the attrition resistant catalyst particles preferred for successful fluid bed operation.

Commercial fluid bed catalysts are preferably microspheroidal particles within the range of about 20 to about 300 microns in average diameter, preferably having about 80% of the particles within the range of about 30 to about 80 microns in diameter. Most preferably, about 25 to about 40% of the particles have an average diameter of less than 45 microns.

It is therefore an object of the invention to provide a process of preparing attrition resistant fluid bed vanadium and phosphorus mixed oxide containing oxidation catalysts.

It is a further object of the invention to provide a process for producing maleic anhydride from 4-carbon atom hydrocarbons utilizing attrition resistant fluid bed vanadium phosphorus mixed oxide catalysts.

SUMMARY OF THE INVENTION

We have found that excellent uniform, attrition resistant microspheroidal fluid bed catalysts, containing the mixed oxides of vanadium and phosphorus, useful in the production of maleic anhydride from 4-carbon atom hydrocarbons can be obtained by the process which includes the steps of:

(a) preparing a vanadium-phosphorus mixed oxide containing catalyst precursor;
(b) densifying the catalyst precursor;
(c) comminuting the catalyst precursor to an average particle size less than about one micron in diameter;
(d) forming microspheroidal fluidizable particles from the densified comminuted catalyst precursor; and
(e) calcining the microspheroidal fluidizable particles under fluidization-type conditions.

The present invention provides the attrition resistant fluid bed catalysts prepared by the above process, and further provides a process for utilizing such attrition resistant catalysts in the production of maleic anhydride in the vapor phase, by the oxidation of 4-carbon atom hydrocarbons with molecular oxygen or an oxygen containing gas.

DETAILED DESCRIPTION OF THE INVENTION

Catalyst precursors of vanadium phosphorus mixed oxide catalysts for hydrocarbon oxidation may be prepared according to methods known in the art.

U.S. Pat. No. 4,002,650 discloses the preparation of vanadium and phosphorus mixed oxide containing catalysts by reacting vanadium and phosphorus compounds in an aqueous solution, with HCl being utilized as a solvating and reducing agent for vanadium. Similar preparational techniques are described in European Patent Appln. Ser. No. 3,431 in which the additional step of comminuting the vanadium-phosphorus precursor to a particle size of 500 to 700 microns (0.5 to 0.7 mm) is disclosed.

U.S. Pat. No. 4,043,943 discloses the preparation of the catalyst precursor in a liquid organic medium, preferably anhydrous, wherein the vanadium compound is reduced and solvated by gaseous HCl followed by reaction with the phosphorus compound.

The preparation of oxidation catalysts containing the mixed oxides of vanadium and phosphorus is disclosed in U.S. Pat. No. 4,244,879 wherein a vanadium compound is at least partially solubilized in an organic liquid medium capable of reducing at least a portion of the vanadium to a +4 valence state, and unsolubilized vanadium having a particle size larger than about 0.1 mm diameter is removed from the medium before addition of a phosphorus-containing compound. The preparation of such catalysts is disclosed in U.S. Pat. No. 4,333,853 wherein partial reduction of a pentavalent vanadium compound is effected in the presence of a phosphorus compound in an organic liquid medium capable of reducing the vanadium.

The catalyst precursor may be recovered from the liquid reaction medium in which it was prepared (preferably an essentially anhydrous maintained organic liquid medium) by conventional methods, such as evaporation, filtration, centrifugation, decanting, and the like. Preferably, the precursor is dried by heating. Alternatively, the recovered precursor, which is still partially wet with the organic liquid, may be treated with a low boiling solvent such as petroleum ether. In another embodiment, excess preparational reaction media may be substantially removed by vacuum filtration. In yet another embodiment, excess water can be introduced into the precursor containing organic liquid reaction medium, allowing an organic layer to separate from the aqueous layer followed by recovery of the catalyst precursor by drying.

After recovery, the catalyst precursor is subjected to densification and comminution. The order in which the catalyst precursor is densified and comminuted is dependent upon the method used for accomplishing these purposes. For example, the catalyst precursor may be densified by tableting or pelleting the catalyst precursor, and thereafter crushing or grinding the densified material to prepare it for formation of the microspheroidal particles. Alternatively, the catalyst precursor may be recovered by drying or spray drying, and thereafter subjected to dry ball milling in order to both densify the precursor material and comminute the catalyst precursor to an average particle size less than about 1 micron in diameter. The steps of densifying and comminuting the catalyst precursor may be repeated such that the final fluidizable catalyst particle has a bulk density equal to or greater than about 0.75 grams per cubic centimeter, preferably greater than or equal to 1 gram per cubic centimeter.

The densified, comminuted catalyst precursor is then formed into microspheroidal fluidizable particles. Formation may be accomplished by the oil drop method, in which an aqueous solution of the catalyst precursor is dropped into a hot oil bath to cause the formation of spheroidal particles. Preferably, the microspheroidal fluidizable particles are formed by spray drying an aqueous slurry of the catalyst precursor.

The formation of fluidizable particles by crushing and screening to form a fluidizable fraction is not suitable for forming attrition resistant catalysts, as the particles easily abraid during fluid bed operation due primarily to their irregular surface texture. Catalysts formed by crushing and screening also are more prone to fracturing, for the same reason.

If spray drying is to be utilized, the catalyst precursor preferably should be uncalcined when introduced into water to form the aqueous slurry. Substantial contacting of the calcined vanadium phosphorus mixed oxide catalyst with water (at less than 100° C.) reduces the activity of the catalyst, particularly if calcined in air.

The solids content of the catalyst precursor containing aqueous slurry should be adjusted to about 25 to about 60 weight % preferably above about 40 weight %. The catalyst precursor-containing aqueous slurry is then spray dried to form uniform, microspheroidal particles having a particle size range of between about 20 to about 300 microns, generally between 20 to about 240 microns. Spray drying may be accomplished by methods known in the art.

Inert diluents or supports may be added to the fluid bed catalyst by the addition of the diluent or support before or during any of the densification, comminution, and formation of the microspheroidal fluidizable particle steps. Such inert diluents or supports may include silica, alumina, alumina silica, titania, niobia, silicon carbide, and the like.

The process of the present invention, however, does not rely solely upon the addition of attrition resistant supports to impart attrition resistance to the catalyst. The particular combination of steps of the present invention results in the formation of an attrition resistant catalyst in which the level of inert supports may be extremely low, or absent. Generally the catalysts of the present invention include at least 70% active material. Preferably, the attrition resistant fluidizable catalyst of the present invention contain at least 80% active material, and most preferably at least 90% active material.

The fluidizable particles prepared above are subjected to calcination under fluidization-type conditions. Fluidization conditions can be determined readily by those of skill in the art, and include the introduction of a gas stream into a catalyst containing fluid bed vessel sufficient to "raise" the catalyst bed and contact substantially all catalyst particles with the gaseous feed, maintaining isothermal temperature control. Other calcination techniques such as cascading calcination, which, similar to fluidization calcination, provide homogeneous gas contacting of the catalyst particles and relatively isothermal temperature control, may be utilized according to the present invention, to result in fluidization-type conditions sufficient to impart attrition resistance to the calcined catalyst. Fluid bed calcination is, however, preferred.

The catalyst is calcined in air or an oxygen containing gas under fluidization-type conditions at a temperature range of about 300° C. to about 450° C. The catalyst may be calcined additionally in the presence of hydrocarbon, an inert gas, steam or both. Preferably, calcination temperature is increased from about 300°–325° C. steadily to 400°–425° C., preferably at a rate of about 0.5° to 5° C. per minute. Calcination times vary depending upon method of preparation, catalyst composition and amount of catalyst, but generally calcination is conducted for a period of time greater than 1 hour.

The catalyst precursor may contain promoter elements, including but not limited to alkali metals, alkaline earth metals, Ti, Cr, W, Ta, U, Co, Mo, Fe, Zn, Hf, Zr, Mn, As, Sb, Te, Bi, Sn, Ge, Nb, Ni, Cu, Cd, Ce, rare earths or mixtures thereof. These may be incorporated into the catalyst precursor in any of the methods known in the art, such as inclusion via the liquid reaction medium prior to or after reduction of the vanadium, or during one or more steps of the preparation of the fluidizable catalyst. The promoter elements may be added to the catalyst as metals, oxides, hydroxides, carbonates, or salts such as halides, nitrates, acetates, formates, butyrates, benzylates, and the like. The molar ratio of promoter elements to vanadium is generally 0.001:1 to 1:1, preferably 0.01:1 to 0.5:1.

Catalysts suitable for the production of maleic anhydride from 4-carbon atom hydrocarbons generally have a phosphorus to vanadium ratio of about 2:1 to about 0.5:1, preferably about 0.8:1 to about 1.3:1. Most preferred is a P/V ratio of about 1.2:1. These catalysts preferably exhibit an average valence for vanadium within the range of +3.5 to +4.6, preferably about +4.

The attrition resistant fluid bed catalyst prepared by the process of the present invention may be utilized in oxidation type fluid bed reactors known in the art.

The hydrocarbon reacted to form maleic anhydride may be n-butane, n-butenes, 1,3-butadiene, or a mixture thereof. Preferred is the use of n-butane or a mixture of hydrocarbons that are produced in refinery streams. The molecular oxygen is most conveniently added as air, but synthetic streams containing molecular oxygen are also suitable. In addition to the hydrocarbon and molecular oxygen other gases may be added to the reactant feed. For example, steam or nitrogen could be added to the reactants.

The ratio of the reactants may vary widely and are not critical. Preferred oxygen/hydrocarbon ratios in the reactor feed are about 4 to about 20 moles of oxygen per mole of hydrocarbon.

The reaction temperature may vary widely and is dependent upon the particular hydrocarbon and catalyst employed. Generally, temperatures of about 325° C. to 500° C. are preferred. The reaction may be conducted at atmospheric, superatmospheric or subatmospheric pressure, although operation at superatmospheric pressure is preferred.

SPECIFIC EMBODIMENTS

Example 1

A fluidizable catalyst of the formula 90% $V_1P_{1.2}O_x$/10% $SiO_2$ (where x is the number of oxygens required to satisfy the valence requirements of the other elements) was prepared by the following method. The catalyst precursor was prepared by introducing 7.3 parts of $V_2O_5$ and about 10.5 parts mixed phosphoric acid into about 100 parts isobutanol with stirring, and refluxing the resulting slurry about 6 hours. The mixed phosphoric acid source contained about 87% orthophosphoric acid, about 12% pyrophosphoric acid and about 1% higher phosphoric acids based upon total weight of phosphoric acid. The resulting vanadium phosphorus catalyst precursor precipitate was filtered and dried. The vanadium phosphorus catalyst precursor was then comminuted to an average particle size less than about 1 micron in diameter and was densified by dry ball milling the precursor.

The comminuted and densified catalyst precursor was introduced into water, and a portion of Nalco Silica Sol (trade designation of Nalco Chemical Co.) was added to the resulting slurry with stirring in an amount necessary to comprise 10% silica by weight based upon total weight of precursor and silica. Solids content of the slurry was above about 45% by weight. The resulting slurry was spray dried to yield uniform, microspheroidal catalyst particles. These fluidizable catalyst particles were charged to a fluid bed vessel and under fluidization conditions, were calcined initially to 300°–325° C. in an air stream. The calcination temperature was then raised about 2° C. per minute to 400°–425° C., with heating at this level for about 1 hour.

The fluidizable, attrition resistant catalysts were utilized in the production of maleic anhydride from n-butane, and were thereafter subjected to the following attrition test. Results of the attrition test are included in Table I below. Microscopic inspection of the attrition tested catalyst particles prepared by the process of the invention revealed very little fragmentation.

Attrition resistance was measured in an apparatus as described in the American Cyanamide Co., "Test Methods for Synthetic Cracking Catalyst", 1957, at page 44. In the test, air is admitted through openings of a perforated plate with sufficient velocity to cause jets of the catalyst to be blown into the main bed of the catalyst at a high velocity. The air velocity through the perforated plate was 1000 feet per second.

Fifty grams of the catalyst, screened through 140 on 230 mesh (0.105 mm on 0.063 mm) was charged to the unit and subjected to the air velocity of 1000 feet per second. The attrited material carried over into the collection flask after 5 hours was weighed and calculated as percent loss in 0–5 hours. The procedure was repeated for 15 more hours and the attrited material was collected over the period (from 5 to 20 hours total), and the percent lost in the 5–20 hour period was calculated as the percentage attrition equal to 100 times the grams recovered in the 5 to 20 hour period divided by the quantity of 50 grams initial charge minus the number of grams recovered in the 0–5 hour period.

Example 2

A fluid bed catalyst having the formula 95% $V_1P_{1.2}O_x$/5% $SiO_2$ was prepared according to the procedure of Example 1, except that only 5% by weight silica was added to the slurry to be spray dried. The resulting fluidizable catalyst was subjected to the calcination procedure described in Example 1. After utilization of the catalyst for the production of maleic anhydride from n-butane, the percent attrition was tested according to the procedure of Example 1. Results of the attrition test are reported in Table 1.

Comparative Example 3

A fluid bed catalyst having the formula 95% $V_1P_{1.2}O_x$/5% $SiO_2$ was prepared according to the procedure of Example 2, except that the fluidizable catalyst particles were subjected to a static calcination (no fluidization) under air. After utilization of the catalyst for the production of maleic anhydride from n-butane, the percent attrition was tested according to the procedure of Example 1. Results of the attrition test are reported in Table 1.

As is reported in the Table, the catalyst which was not subjected to fluidization-type conditions during calcination has much poorer attrition resistance as compared to the fluid bed calcined catalysts.

It is to be noted that the attrition test utilized is an accelerated test, and the attriting forces to which the catalyst is subjected are several hundred times greater than the forces which would be encountered in normal fluid bed operation. In fact, percent attrition was found to fall logarithmically upon reduction of the air velocity. For example, a catalyst was tested which exhibited 8.3% attrition (weight loss) during 0–5 hours at an air velocity of 1000 feet per second, and a catalyst prepared in the same batch was subjected to 500 feet per second velocities, exhibiting only a 0.8% weight loss in the 0–5 hour period.

EXAMPLE 4

A fluid bed catalyst having the formula 100% $V_{1.0}P_{1.2}O_x$ was prepared according to the procedure of Example 1, except that no silica was added to the slurry. During the preparation the catalyst precursor was comminuted and densified by dry ball milling. The spray dried particles were subjected to calcination under fluidization conditions in air, initially at 300° C. with heating at about 2° C. per minute until 425° C. was reached, and with calcination continuing at 425° C. for about 45 minutes.

The fluid bed calcined catalyst was subjected to the attrition test according to the procedure of Example 1 both before and after utilization of the catalyst for the production of maleic anhydride from n-butane, and the results of the tests are reported in Table 1.

Comparative Example 5

A fluid bed catalyst having the formula 100% $V_1P_{1.2}O_x$ was prepared according to the procedure of Example 4, except that the fluidizable particles were subjected to a static calcination (no fluidization) under air for about $2\frac{1}{2}$ hours. The calcined catalyst was subjected to the attrition test according to the procedure of Example 1, and test results are reported in Table 1.

The most significant test period is considered to be the 5-20 hour test period. As is demonstrated by the results reported in Table 1, the process of the present invention produces a much more highly attrition resistant catalyst than a procedure which omits fluidization of the catalyst particles during calcination. The catalyst prepared according to the process of the present invention exhibited a much lower percentage weight loss as a result of the attrition test.

Comparative Example 6

A fluid bed catalyst of the formula 100% $V_1P_{1.2}O_x$ was prepared by a procedure which omitted the densification of the catalyst precursor, the comminution step being conducted by the ball milling of an aqueous slurry of the catalyst precursor, preventing the densification.

In addition, the spray dried catalysts were subjected to a static calcination in air, at 400° C. for 1 hour. The resulting fluidizable catalyst was subjected to the attrition test according to the procedure of Example 1, and the results of the test are reported in Table 1. As is demonstrated by the results reported in the Table, the omission of the densification step and the fluid bed calcination resulted in the majority of the catalyst being attrited away even in the first 5 hour test period.

Comparative Example 7

A fluid bed catalyst of the formula 100% $V_1P_{1.2}O_x$ was prepared by a procedure which omitted the densification of the catalyst precursor, the comminution step being conducted in an air mill (in which dry particles impinge upon themselves and shatter). The spray dried catalysts were additionally subjected to static calcination. The resulting fluidizable catalyst was subjected to the attrition test of Example 1, and as shown in Table 1, the majority of the catalyst was attrited away in the first 5 hour test period.

Example 8

In order to demonstrate the suitability of the attrition resistant fluid bed catalysts prepared by the process of the present invention for the fluid bed production of maleic anhydride, the catalyst prepared in Example 4 was used to produce maleic anhydride from n-butane in a fluid bed reactor consisting of about a 61 cm length of stainless steel tubing having an inner diameter of about 4.1 cm, having a stainless steel sparger at the bottom of the tube to act as a gas (air) distributor, with an axial 0.64 cm outer diameter thermowell and a separate hydrocarbon inlet at the bottom of the tube. The reactor was fitted with internal gas redistributing baffles. Gas preheating and reactor temperature control was accomplished by placement of the reactor unit in a thermostated fluidized sand bath.

Flasks for receiving the product maleic anhydride were air cooled, and tail gases were routed to a gas chromatograph for analysis. The results are stated in terms as follows:

$$\text{Single Pass Yield} = \frac{\text{Moles of Maleic Anhydride Formed}}{\text{Moles of Butane Fed}} \times 100$$

$$\text{Total Conversion} = \frac{\text{Moles of Butane Reacted}}{\text{Moles of Butane Fed}} \times 100$$

$$\text{Selectivity} = \frac{\text{Single Pass Yield}}{\text{Total Conversion}}$$

The throughput of hydrocarbon feed in the production of maleic anhydride, or the working rate imposed upon the catalyst is expressed as WWH (weight of feed/weight of catalyst/hour) and was adjusted to 0.50.

The catalyst was initially activated, and at 116 hours of operation exhibited a Total Conversion of 90.1% at a Selectivity to maleic anhydride of 62.2% and a Single Pass Yield of maleic anhydride of 56.1%.

As can be seen from the results reported in Table I and the Examples above, fluid bed catalysts containing the mixed oxides of vanadium and phosphorus may be prepared according to the present invention, such catalysts being highly attrition resistant and useful in the production of maleic anhydride from 4-carbon atom hydrocarbons. The fluid bed catalysts thus prepared are suitable for use as commercial fluid bed catalysts.

Thus it should be apparent to those skilled in the art that the subject invention accomplishes the objects set forth above. It is to be understood that the subject invention is not to be limited by the examples set forth herein. These have been provided merely to demonstrate operability, and the selection of methods of preparation of the vanadium and phosphorus mixed oxide containing catalyst precursors, promoter elements, if any, inert diluents or supports, if any, methods of comminution and densification, calcination conditions, hydrocarbon feedstocks and reaction conditions can be determined from the total specification disclosure provided without departing from the spirit of the invention herein disclosed and described, the scope of the invention including modifications and variations that fall within the scope of the attached claims.

TABLE I

| Example No. | When Tested[a] | % Attrition[b] 0-5 Hours | 5-20 Hours |
|---|---|---|---|
| 1 | After Use | 5.5 | 10.1 |
| 2 | After Use | 3.3 | 7.5 |
| C3 | After Use | 6.4 | 25.3 |
| 4 | Before Use | 1.4 | 4.1 |
|   | After Use | 3.2 | 12.2 |
| C5 | Before Use | 7.2 | 32.1 |
| C6 | Before Use | 53.8 | 10.4 |
| C7 | Before Use | 69.8 | 11.0 |

[a]Before or after use to produce maleic anhydride from n-butane.
[b]% weight loss during period of the test.

We claim:

1. A process for the preparation of an attrition resistant microspheroidal fluid bed oxidation catalyst containing the mixed oxides of vanadium and phosphorus, comprising:

(a) preparing a vanadium phosphorus mixed oxide containing catalyst precursor;
(b) densifying the catalyst precursor;
(c) comminuting the catalyst precursor to an average particle size less than about one micron in diameter;
(d) forming fluidizable particles having a bulk density greater than or equal to 0.75 grams per cubic centimeter from the densified, comminuted catalyst precursor;
(e) calcining the fluidizable particles under fluidization-type conditions.

2. A process as in claim 1, wherein said catalyst precursor is prepared in an organic liquid.

3. A process as in claim 1, wherein said catalyst precursor is prepared in an organic liquid slurry.

4. A process as in claim 1, wherein a substantial portion of said catalyst precursor is comminuted to an average particle size of less than about one-half micron average diameter.

5. A process as in claim 1, wherein said fluidizable particles are formed by introducing the catalyst precursor into water to form an aqueous slurry and spray drying said slurry to form microspheroidal catalyst particles.

6. A process as in claim 5, wherein said aqueous slurry has a solids content of about 25 to about 60 weight percent.

7. A process as in claim 1, wherein a substantial portion of said fluidizable particles have a particle size of less than 300 microns.

8. A process as in claim 1, wherein the catalyst precursor is densified and comminuted by ball milling the dried catalyst precursor.

9. A process as in claim 1, wherein the bulk density of said fluidizable catalyst is greater than or equal to about 1 gram per cubic centimeter.

10. A process as in claim 1, wherein said fluidizable catalyst additionally comprises promoter elements selected from the group consisting of alkali metals, alkaline earth metals, Ti, Cr, W, Ta, U, Co, Mo, Fe, Zn, Hf, Zr, Mn, As, Sb, Te, Bi, Sn, Ge, Nb, Ni, Cu, Cd, Th, Ce, rare earths or mixtures thereof.

11. An attrition resistant, fluidizable microspheroidal oxidation catalyst, comprising the mixed oxides of vanadium and phosphorus characterized by an average valence state of vanadium from about +3.5 to about +4.6 and a phosphorus to vanadium ratio of about 0.5:1 to about 2:1 wherein said catalyst is prepared by:
(a) preparing a vanadium phosphorus mixed oxide containing catalyst precursor;
(b) densifying the catalyst precursor;
(c) comminuting the catalyst precursor to an average particle size less than about one micron in diameter;
(d) forming fluidizable particles having a bulk density greater than or equal to 0.75 grams per cubic centimeter for the densified, comminuted catalyst precursor;
(e) calcining the fluidizable particles under fluidization-type conditions.

12. A catalyst as set forth in claim 11, wherein said catalyst additionally comprises promoter elements selected from the group consisting of alkali metals, alkaline earth metals, Ti, Cr, W, Ta, U, Co, Mo, Fe, Zn, Hf, Zr, Mn, As, Sb, Te, Bi, Sn, Ge, Nb, Ni, Cu, Cd, Th, Ce, rare earths or mixtures thereof.

13. A catalyst as in claim 11, wherein said catalyst precursor is prepared in an organic liquid.

14. A catalyst as in claim 11, wherein said catalyst precursor is prepared in an organic liquid slurry.

15. A catalyst as in claim 11, wherein a substantial portion of said catalyst precursor is comminuted to an average particle size of less than about one-half micron average diameter.

16. A catalyst as in claim 11, wherein said fluidizable particles are formed by introducing the catalyst precursor into water to form an aqueous slurry and spray drying said slurry to form microspheroidal catalyst particles.

17. A catalyst as in claim 16, wherein said aqueous slurry has a solids content of about 25 to about 60 weight percent.

18. A catalyst as in claim 11, wherein a substantial portion of said microspheroidal particles have a particle size of less than 300 microns.

19. A catalyst as in claim 11, wherein the catalyst precursor is densified and comminuted by ball milling the dried catalyst precursor.

20. A catalyst as in claim 11, wherein the bulk density of said fluidizable catalyst is greater than or equal to about 1 gram per cubic centimeter.

* * * * *